United States Patent [19]

Thiel

[11] Patent Number: 4,819,834

[45] Date of Patent: Apr. 11, 1989

[54] APPARATUS AND METHODS FOR DELIVERING A PREDETERMINED AMOUNT OF A PRESSURIZED FLUID

[75] Inventor: Charles G. Thiel, St. Paul, Minn.

[73] Assignee: Minnesota Mining and Manufacturing Company, St. Paul, Minn.

[21] Appl. No.: 905,306

[22] Filed: Sep. 9, 1986

[51] Int. Cl.⁴ ............................................. G01F 11/10
[52] U.S. Cl. ................................ 222/355; 222/402.16; 222/402.2; 128/200.23
[58] Field of Search ................ 222/374, 402.2, 402.24, 222/402.16, 335, 453, 355; 128/200.23; 251/353, 354; 137/269; 239/337

[56] References Cited

U.S. PATENT DOCUMENTS

| | | | |
|---|---|---|---|
| 2,886,217 | 5/1959 | Thiel | 222/394 |
| 2,968,427 | 1/1961 | Meshberg | 222/394 |
| 3,049,269 | 8/1962 | Gawthorp | 222/307 |
| 3,052,382 | 9/1962 | Gawthorp | 222/335 |
| 3,104,785 | 9/1963 | Beard, Jr. | 222/207 |
| 3,142,420 | 7/1964 | Gawthrop | 222/335 |
| 3,173,585 | 3/1965 | Kahn | 222/402.2 |
| 3,187,962 | 6/1965 | Meshberg | 222/394 |
| 3,456,644 | 7/1969 | Thiel | 128/173 |
| 3,456,646 | 7/1969 | Phillips et al. | 128/173 |
| 3,464,596 | 9/1969 | Meshberg | 222/402.2 |
| 3,499,584 | 3/1970 | Warren | 222/402.2 |
| 3,565,070 | 2/1971 | Hanson et al. | 128/173 |
| 3,591,059 | 7/1971 | Stearns | 222/402.20 |
| 3,598,294 | 8/1971 | Hedrick et al. | 222/402.2 |
| 3,708,090 | 1/1973 | Harris | 222/402.22 |
| 3,727,806 | 4/1973 | Wilmot | 222/402.2 |
| 3,738,542 | 6/1973 | Ruscitti | 222/402.16 |
| 3,814,297 | 6/1974 | Warren | 222/402.13 |
| 4,142,652 | 3/1979 | Platt | 222/402.2 |
| 4,271,875 | 6/1981 | Meshberg | 141/3 |
| 4,407,481 | 10/1983 | Bolton et al. | 251/353 |
| 4,413,755 | 11/1983 | Brunet | 222/402.2 |
| 4,427,137 | 1/1984 | Dubini | 222/402.2 |
| 4,441,634 | 4/1984 | Meshberg | 222/402.16 |
| 4,597,512 | 7/1986 | Wilmot | 222/402.2 |
| 4,629,099 | 12/1986 | Jones | 222/453 |

Primary Examiner—Kevin P. Shaver
Assistant Examiner—Kenneth Noland
Attorney, Agent, or Firm—Donald M. Sell; Walter N. Kirn; Dale E. Hulse

[57] ABSTRACT

The present invention relates to metering valves and methods for repeatedly delivering a precise amount of a pressurized fluid such as an aerosol. Each metering valve is configured such that the metering chamber exists only upon actuation of the valve stem to dispense a dosage. Thus, the metering chamber is created, filled with aerosol formulation, and emptied during the brief moment that the valve stem is depressed and subsequently released by the user to dispense a dosage. Alternative embodiments of the present invention also include mechanisms for pressure filling an aerosol container through such a metering valve.

61 Claims, 10 Drawing Sheets

APPARATUS AND METHODS FOR DELIVERING A PREDETERMINED AMOUNT OF A PRESSURIZED FLUID

BACKGROUND

1. The Field of the Invention

The present invention relates to valve apparatus and methods for delivering a predetermined amount of a pressurized fluid. In particular, the present invention relates to positive-fill metering valves and methods for repeatably delivering a precise amount of an aerosol.

2. The Prior Art

Various different types of metering valves have been developed in the art for dispensing aerosols from aerosol containers. Such metering valves have found particular utility in the administration of medical formulations which can be mixed with a liquified gas propellant and delivered to a patient in an aerosol.

As will be appreciated, when aerosol container devices are used to dispense medications, it is often quite important that a precise, predetermined amount of the medication is dispensed with each successive dose, so that each dose delivered will contain the proper amount of medication needed to effect the desired physiological response. For example, if the aerosol medication dispensed is intended to prevent an asthma attack in an asthma patient, an incomplete dosage delivered to the patient could well mean that the attack would not be arrested. As will be appreciated by those of ordinary skill in the art, there are many other instances where the delivery of a precise and a reliable amount of medication is very important and very desirable.

Thus, in order to provide some control over the amount of aersol formulation released in each dosage from the aerosol container, a metering valve was developed having a metering tank or chamber to define the amount of formulation dispensed in each dosage. Obviously, the precise dosage delivered from such a prior art metering valve is dependent upon the dimensions and other physical characteristics of the metering tank as well as the physical conditions to which the formulaton is subjected within the metering tank.

In the course of normal operation, the metering tank of a typical prior art metering valve is full of the aerosol formulation before the valve stem is depressed to release a dose. Thus, the metering tank must be refilled with formulation after discharging one dose so as to ready the metering valve for the discharge of the next dose. As a result, except for the brief moment during dosage discharge, the metering tank is full of formulation at all times so as to be ready to dispense a dose as the user's needs require. Further, the passageways leading from the bulk of formulation in the aerosol container to the metering tank are often narrow and tortuous. Unfortunately, many disadvantages have been experienced in the usage of prior art metering valves having these features.

For example, because the prior art metering tank is filled with aerosol formulatoin at all times in between dosages, the formulation in the metering tank is often adversely affected. First, a loss of prime may result. Because of temperature changes, vibrations, or the particular orientation of the metering valve during storage, the formulation may drain out of the metering tank in between dosages, thereby resulting in a loss of its prime. Even upon simple standing for extended periods of time between dosages, the metering tank may become empty, thereby requiring activation of the valve stem several times before the valve will deliver a full dose of formulation. As will be appreciated, such a purging procedure is wasteful of the aerosol formulation, and there is no way of determining how many doses must be dispensed before the valve is fully primed and prepared once again to deliver a full dose of formulation. Moreover, when loss of prime occurs, a vapor lock may form in the metering tank which prevents further formulation from entering into the metering tank.

Another related disadvantage which is often encountered in such prior art metering valves is the erratic delivery of medication where suspension formulations are involved. Many medications are comprised of a suspension of various chemical components which will either sink or float in the liquified gas propellant used to form the aerosol. Thus, depending upon the relative density of the various components in the aerosol medication, certain components in the medication may either float or sink into or out of the metering tank, depending upon the storage position of the metering valve. As a result, the dosage subsequently delivered to the patient will not contain the proper composition and concentration of components intended to be delivered. Further, if the aerosol container is shaken, gas bubbles may form. If these bubbles find their way into the metering tank, the next dose delivered will contain a mixture of formulation and bubbles instead of a full dose of formulation.

Still another problem often encountered with prior art metering valves is the undesirable phenomenon known as "tail-off." Tail-off refers to the fact that, when the aerosol container gets close to being empty, dosage delivery becomes erratic. Thus, the last few dosages delivered often contain less than the full amount of formulation.

Yet another problem encountered in the usage of prior art metering valves is the undesirable phenomenon known as "holdup." Holdup refers to the excess formulation which is left in the aerosol container after the last possible dose has been discharged from the metering valve. Naturally, when the formulation being delivered is significantly expensive or valuable, the holdup or amount of formulation left in the aerosol container and subsequently discarded becomes important. Unfortunately, the holdup experienced in many prior art aerosol dispensing devices often represents many doses which are ultimately wasted.

In an attempt to address some of the problems of the prior art, a retaining cup or drainage cup has been incorporated into some metering valves. However, such retaining cups have not satisfactorily solved the problems of loss of prime, erratic delivery of medication comprising suspension formulations, tail-off, and holdup. For example, temperature changes and vibrations within the metering valve may still cause the formulation to be expelled from the retaining cup, thereby resulting in erratic medication delivery. Further, retaining cups still experience significant tail-off and holdup.

From the foregoing, it will be appreciated that it would be a significant advancement in the art to provide metering valves which do not experience significant loss of prime or deliver erratic compositions and concentrations of medication. Further, it would be a significant advancement in the art to provide metering valves wherein the problems of tail-off and holdup are substantially eliminated. Moreover, it would be an advancement in the art to provide metering valves which deliver a precise, predetermined amount of a pressurized fluid or aerosol such that each successive dose is of virtually the same amount and composition, thereby providing for repeatable dosages even after standing or storage for a significant period of time. Such metering valves and methods for dispensing pressurized fluids such as aerosols are disclosed and claimed herein.

BRIEF SUMMARY AND OBJECTS OF THE INVENTION

The present invention relates to valves and methods for delivering a predetermined amount of a pressurized fluid or formulation, which valves and methods employ a metering chamber which remains virtually empty during storage and standing, and fills with formulation only as the valve stem is actuated to discharge a dose. In this regard, the volume inside the metering chamber which is to be filled with formulation exists only when the valve is actuated to discharge a dose, and thus does not serve to store the next successive dose of formulation as is done in the prior art.

One presently preferred embodiment of the present invention is described as follows. A valve housing is provided to house the various components of the metering valve, and a metering chamber is formed within the valve housing. A valve stem is displaceably mounted within the valve housing and has a portion which is generally internal to the valve housing and a portion which is generally external thereto. The internal portion of the valve stem is configured substantially the same as the wall defining the metering chamber such that, when the valve stem is in a resting of inoperational position, the internal portion of the valve stem occupies substantially the entire volume of the metering chamber, with just sufficient space between the internal portion of the valve stem and the wall of the metering chamber to allow for the passage of pressurized fluid during actuation of the valve.

The external portion of the valve stem extends through an opening formed in the valve housing such that substantially all of the external portion of the valve stem is exterior to the metering chamber when the valve stem is in the resting position. Importantly, the internal portion of the valve stem has a larger circumference than the external portion of the valve stem. Thus, when the valve stem is actuated by displacing the external portion of the valve stem towards the metering chamber so as to position at least a part of the external portion of the valve stem within the metering chamber, a filling volume is created within the metering chamber.

Means are provided for immediately filling the filling volume of the metering chamber with the pressurized fluid as soon as the filling volume is created, and for terminating the supply of pressurized fluid to the filling volume once a predetermined amount of the pressurized fluid has been introduced into the filling volume. The filling volume thus defines the amount of pressurized fluid to be delivered in a single dosage. As the external portion of the valve stem continues through the metering chamber, means are actuated for releasing the pressurized fluid from the metering chamber and delivering the pressurized fluid to the patient or other area desired.

Thus, by configuring the external portion of the valve stem smaller than the internal portion of the valve stem, the valve stem itself creates the filling volume as it enters the metering chamber, and the pressurized fluid or formulation to be delivered enters the filling volume of the metering chamber only upon actuation of the valve stem to deliver a dose. Subsequently, immediately after the desired amount of formulation is introduced into the filling volume, the formulation dosage is expelled from the metering chamber. It will therefore be appreciated that the present invention does not involve the usage of a metering chamber which is filled immediately after the discharge of one dose so as to contain the next dose to be dispensed. Because the unique design of the present invention avoids filling the metering chamber during storage or standing, the problems of the prior art are substantially avoided.

In another presently preferred embodiment of the present invention, the metering valve also includes a piston mounted within the valve housing. This piston is configured so as to receive the internal portion of the valve stem as it is actuated and moved through the valve housing, thereby creating a positive filling pressure within the metering chamber to encourage the formulation to enter the filling volume immediately upon its creation. Thus, this presently preferred embodiment of the present invention has been termed a "positive-fill metering valve" for pressurized fluids such as aerosols.

It is, therefore, an object of the present invention to provide metering valves and methods for delivering a predetermined amount of a pressurized fluid or formulation employing a metering chamber which is filled with formulation only upon actuation of the valve stem, and wherein the formulation introduced into the metering chamber is immediately dispensed after the metering chamber has been filled.

Another object of the present invention is to provide metering valves and methods for delivering a predetermined amount of a pressurized fluid wherein a piston is employed to provide a positive fill pressure for the metering chamber upon actuation of the valve stem.

A further object of the present invention is to provide metering valves and methods for delivering a predetermined amount of a pressurized fluid wherein the metering valve does not need to be primed and wherein the metering valve does not suffer from the prior art problem of losing its prime, thereby avoiding the necessity of actuating the valve repeatably in order to deliver a full does from the valve.

Still another object of the present invention is to provide metering valves and methods for delivering a predetermined amount of a pressurized fluid or formulation wherein erratic delivery of suspension type formulations or medicatons is substantially avoided, such that a dosage which is uniform in amount and composition is accurately delivered each successive time the valve is actuated.

Yet another object of the present invention is to provide metering valves and methods for delivering a predetermined amount of a pressurized fluid or formulation wherein the problems of tail-off are substantially avoided such that uniform and accurate doses of formulation are delivered even as the supply of formulation begins to dwindle.

Still yet another object of the present invention is to provide metering valves and methods for delivering a predetermined amount of a pressurized fluid or formulation wherein the amount of holdup or formulation wasted is limited to less than one dose of the formulation.

Another object of the present invention is to provide metering valves and methods for repeatably delivering a precise amount of an aerosol, such as aerosols which are used for medicinal purposes.

A further object of the present invention is to provide metering valves which are relatively simple to manufacture and which may be adapted to provide for pressure filling of the valves if desired.

These and other objects and features of the present invention will become more fully apparent from the following description and appended claims, taken in conjunction with the accompanying drawings.

DETAILED DESCRIPTION OF THE PREFERRED EMBODIMENTS

Initially, it should be pointed out that the following discussion is set forth in terms of an aerosol metering valve used to dispense an aerosol formulation fro m an aerosol container. However, it will be understood that the metering valves and methods of the present invention have application to virtually any pressurized fluid where there is the requirement for the delivery of a precise, metered dose. In the presently most preferred application, the present invention finds particular utility in dispensing aerosol formulations for medicinal use, such as formulations for treating asthma and arresting asthma attacks.

In the administration of medicinal formulations, the apparatus and methods of the present invention may be used to administer virtually any drug into a body cavity of a patient, such as the mouth, nose, anus, vagina, ears or eyes, or onto any skin area of the patient. For example, the present invention may be used to administer oral inhalation drugs or nasal sprays. However, from the foregoing, it will be appreciated that the present invention is not limited to medicinal applications and may be used wherever a precise amount of pressurized fluid is to be precisely delivered to a given area.

Figure 1:
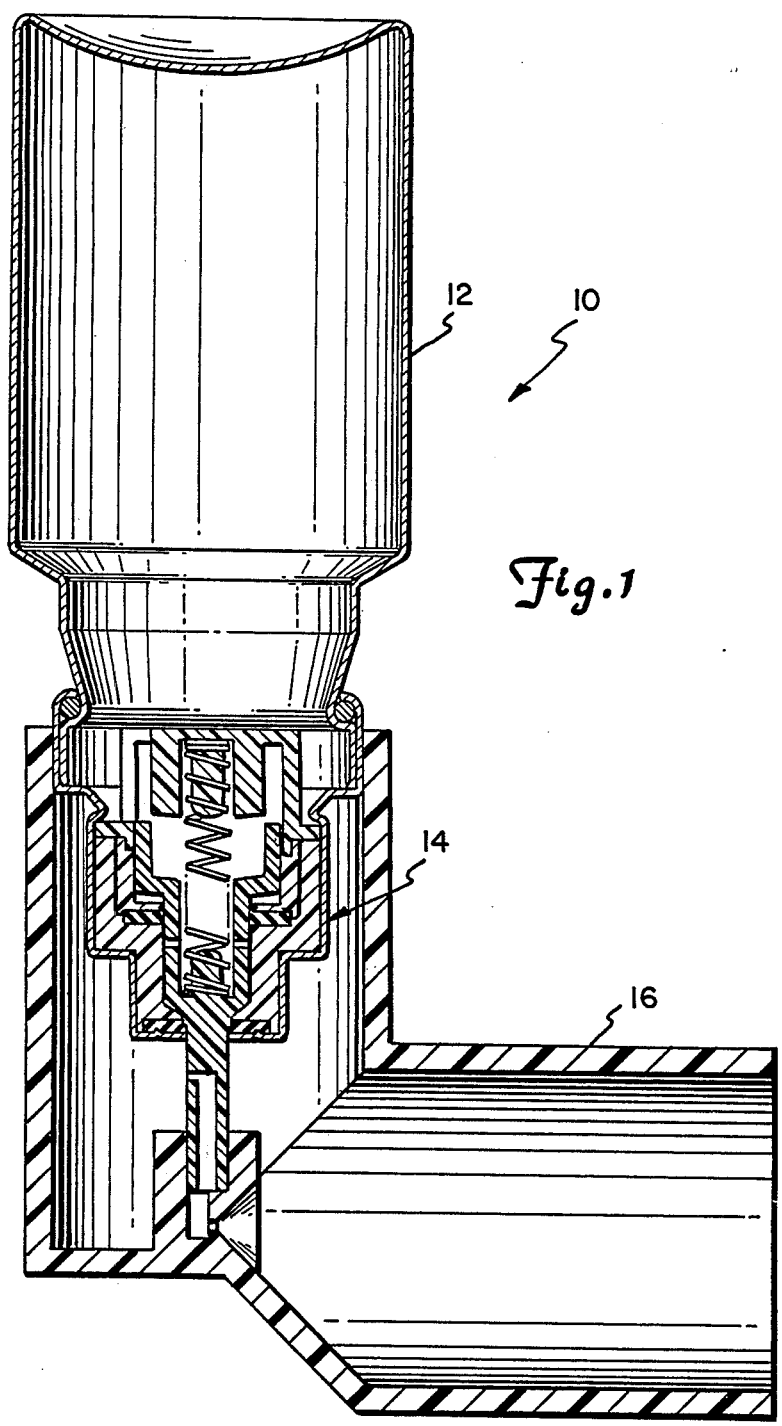
FIG. 1 is a cross-sectional illustration of a pressurized fluid dispensing apparatus employing one presently preferred embodiment of a metering valve in an accordance with the present invention.

Reference will now be made to the drawings wherein like parts are designated with like numerals throughout. Referring first to FIG. 1, an aerosol dispensing apparatus, generally designated 10, is illustrated which incorporates one presently preferred embodiment of a metering valve (designated 14) in accordance with the present invention. As seen in FIG. 1, the top end of the housing of metering valve 14 is crimped around the end of a conventional aerosol container 12, while a conventional discharge piece 16 is mounted around the bottom of metering valve 14. Thus, in the embodiment shown in FIG. 1, the apparatus is oriented such that the aerosol formulation is dispensed downwardly from the aerosol container 12, into the metering valve 14, and through discharge piece 16 where it is delivered to the patient.

As will be appreciated, discharge piece 16 provides for directing the aerosol dispensed towards the appropriate body cavity or skin area. For example, discharge piece 16 may function as a mouthpiece which is inserted into the mouth of the patient so as to provide for oral administration of the aerosol formulation.

The orientation of metering valve 14 shown in FIG. 1, whereby the aerosol formulation is dispensed downwardly, is presently preferred, especially where it is desirable to minimize holdup to less than one dosage, as will be explained in more detail later. However, it will be appreciated that the metering valves of the present invention may be stored in virtually any position, including the position opposite to that shown in FIG. 1.

It will further be appreciated that the aerosol dispensing apparatus 10 shown in FIG. 1 is merely one example of how the metering valves of the present invention can be incorporated into dispensing apparatus, and should be considered as only exemplary in this regard. Further, it should be recognized that the usage of a discharge piece 16 is purely optional, and that the aerosol formulation or other pressurized fluid could merely be released from the valve stem of the metering valve without employing such a discharge piece.

In each of FIGS. 2-10, a metering valve alone is illustrated (for ease of illustration) without the aerosol container or discharge piece shown in FIG. 1. Thus, it will be understood that each of the valves of FIGS. 2-10 is shown in its uncrimped state, and may be combined with an aerosol container and a discharge piece as shown in FIG. 1.

Figure 2:
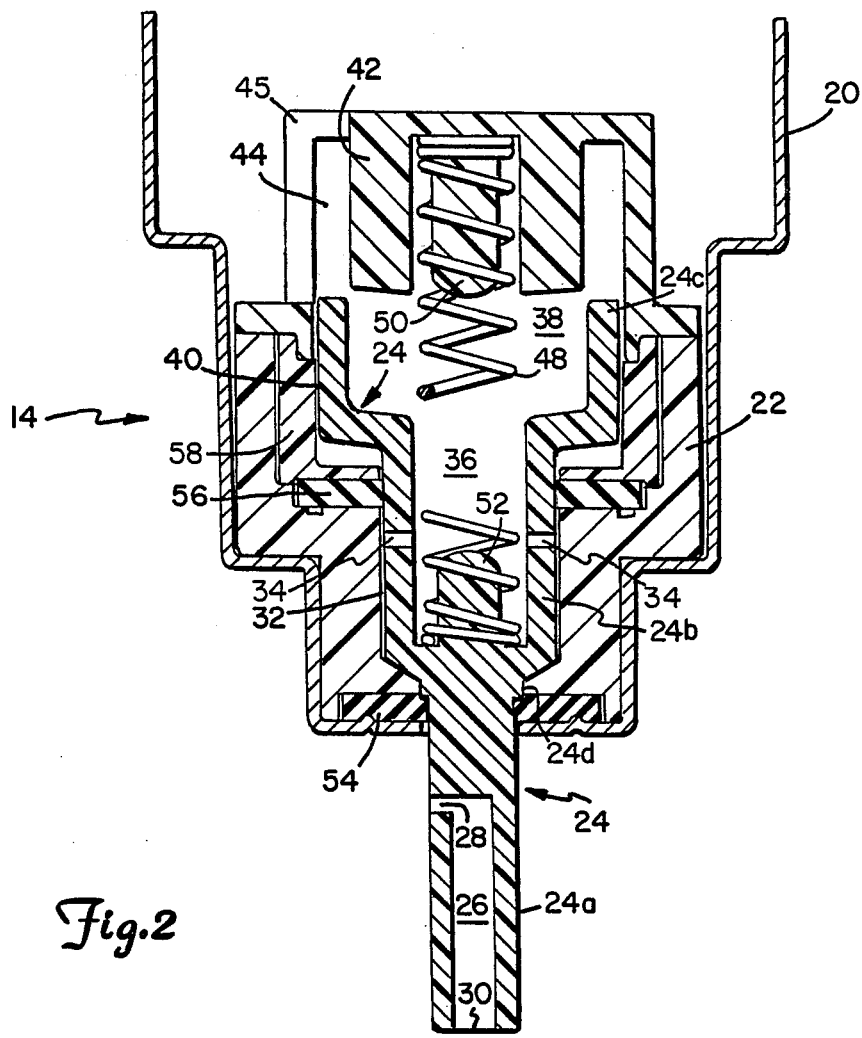
FIG. 2 is an enlarged cross-sectional view of the metering valve illustrated in FIG. 1, with the valve being in a resting or inoperational position.

Referring now to FIG. 2, the internal structure of metering valve 14 can be more easily viewed. At this point, it should be noted that the valve is positioned in the resting or inoperational position in the illustration of FIG. 2. Metering valve 14 preferably has a circular cross section along the plane perpendicular to the page of FIG. 2.

As seen in FIG. 2, metering valve 14 includes a valve housing or ferrule 20 which serves to house the various components of the metering valve. It is the top portion of valve housing 20 which is attached to the aerosol container (as was best illustrated in FIG. 1). A valve body 22 is seated within valve housing 20 and serves to secure a valve stem, generally designated 24 in FIG. 2, within valve housing 20.

In one presently preferred embodiment, valve stem 24 comprises three distinct portions: an external portion 24a, a first internal portion 24b, and a second internal portion 24c. The various portions of the valve stem 24 have been named for their locations with respect to valve housing 20. Thus, external portion 24a is generally external to valve housing 20, while internal portions 24b and 24c are generally internal to valve housing 20.

Referring still to FIG. 2, external portion 24a of the valve stem has formed therein a passageway or bore 26 which is generally L-shaped. In this regard, bore 26 has an opening 28 through the side wall of external portion 24a and an opening 30 at the bottom end of external portion 24a as shown in FIG. 2. As will be explained in more detail hereinafter, bore 26 provides means for releasing the aerosol from the metering valve once a dosage has been metered therewithin.

The first internal portion 24*b* of the valve stem is configured so as to have substantially the same configuration as the adjacent wall of valve body 22. Further, as seen in FIG. 2, first internal portion 24*b* has a significantly larger circumference than external portion 24*a*. As will be explained in more detail hereinafter, valve stem 24 is vertically displaceable within valve housing 20 so as to allow a part of external portion 24*a* to be inserted into valve housing 20. (See FIGS. 3, 4, and 5 in this regard.) When this is done, a space is created between the wall of valve body 22 and valve stem 24 within valve housing 20. This space defines the metering chamber of the metering valve, and thus the dosage of formulation to be delivered.

Referring still to FIG. 2, it is noted that first internal portion 24*b* is configured so as to be slightly smaller than the surrounding wall of valve body 22 so as to form a narrow annular passageway 32 which is just large enough to allow for the passage of aerosol formulation between internal portion 24*b* and valve body 22. (It will be understood that the width of narrow annular passageway 32, as well as passageways 40 and 46 to be discussed later, is exaggerated in the drawings for ease of illustration, and is just sufficient to allow for the passage of aerosol formulation therethrough.) One or more openings or passageways 34 are formed in the side wall of first internal portion 24*b*, and provide for fluid communication between annular passageway 32 and a hollow interior 36 formed within internal portion 24*b*, when the valve stem 24 is positioned as shown in FIG. 2.

When the valve stem is in the resting position shown in FIG. 2, internal portion 24*b* occupies substantially the entire volume of the metering chamber, with the sole exception of narrow passageway 32. Thus, in the resting position, the metering chamber within valve housing 20 is virtually nonexistent.

Second internal portion 24*c* of the valve stem also has a hollow interior 38 (which communicates with hollow interior 36) and is configured so as to have a significantly larger circumference than first internal portion 24*b*. Thus, the overall configuration of valve stem 24 is somewhat akin to a telescopic configuration, with the circumference of each successive portion becoming smaller as the bottom of valve stem 24 is approached in FIG. 2. As with the first internal portion 24*b*, a narrow annular passageway 40 is provided between second internal portion 24*c* and the surrounding structure of the valve so as to allow for the passage of aerosol formulation therethrough.

Referring still to FIG. 2, a piston 42 is mounted within valve housing 20 and is configured so as to receive second internal portion 24*c* and thereby provide a positive filling pressure within the metering valve, as will be explained in more detail hereinafter. The supporting structure 45 for piston 42 has formed therein one or more ports 44 for providing fluid communication between the aerosol container and the hollow interior 38 of second internal portion 24*c*. Furthermore, piston 42 is configured such that upon engagement of second internal portion 24*c*, there is a narrow annular passageway 46 provided therebetween so as to allow for the passage of excess aerosol formulation through passageway 46. (See FIGS. 4 and 5 in this regard.)

Referring again to FIG. 2, a spring 48 is provided within the hollow interiors 36 and 38 of the valve stem. Preferably, spring 48 is attached at one end thereof to a nipple 50 formed on piston 42 and at the other end thereof to a nipple 52 formed inside first internal portion 24*b* . As seen in FIG. 2, spring 48 serves to bias valve stem 24 in a direction away from piston 42.

It will be appreciated that spring 48 and nipples 50 and 52 are merely one example of means for biasing valve stem 24 away from piston 42, and that other biasing structure could be used to accomplish this purpose. Further in this regard, it will be appreciated that spring 48 could be positioned within the metering valve without the use of nipples. Thus, any other suitable means for biasing valve stem 24 away from piston 42 may be used in accordance with the present invention.

Formed around the portion of valve stem 24 which extends through the bottom of valve housing 20 is a gasket or seal 54 which serves to provide a fluid tight seal between valve stem 24 and the interior of valve housing 20. In one preferred embodiment, a slight shoulder 24*d* is formed around the valve stem so as to enhance the fluid tight seal between valve stem 24 and gasket 54. A gasket or seal 56 is also formed around the second internal portion 24*b*, and provides a means for terminating the flow of aerosol formulation from the aerosol container to the metering chamber during operation of the valve, as will be explained in more detail hereinafter. An annular gasket retainer 58 serves to hold gasket 56 in place and also forms passageway 40 with second internal portion 24*c*.

The operation of the embodiment of FIG. 2 and one presently preferred embodiment of the methods of the present invention will now be explained with reference to FIGS. 3, 4, and 5. In this regard, it should be noted that FIGS. 3, 4, and 5 illustrate the relative positions of the valve components as the valve stem 24 is depressed by the user to release a dosage of aerosol formulation. In this regard, FIG. 3 represents the filling or metering position, FIG. 4 represents the completely filled or metered position, and FIG. 5 represents the firing or discharging position.

Reference is now made to FIG. 3 illustrating the filling position of the metering valve 14. The valve stem 24 is first depressed upwardly by the user against the tension of spring 48. (If a discharge piece 16 as illustrated in FIG. 1 is attached to the valve stem 24, such depression is accomplished merely by pushing discharge piece 16 upwardly towards metering valve 14.)

As the valve stem 24 is displaced upwardly, the upper part of external portion 24a of the valve stem is introduced into valve housing 20 such that an annular space 60 is formed between valve body 22 and valve stem 24. This annular space is the metering chamber which will hold the aerosol formulation to be dispensed. Because of the unique configuration of the metering valves of the present invention, metering chamber 60 is virtually nonexistent until valve stem 24 is depressed upwardly. Thus, as the valve stem is depressed, a filling volume is formed within metering chamber 60, which filling volume increases as the valve stem progresses upwardly until the filling volume reaches the volume depicted in the completely filled position of FIG. 4.

Figure 3:
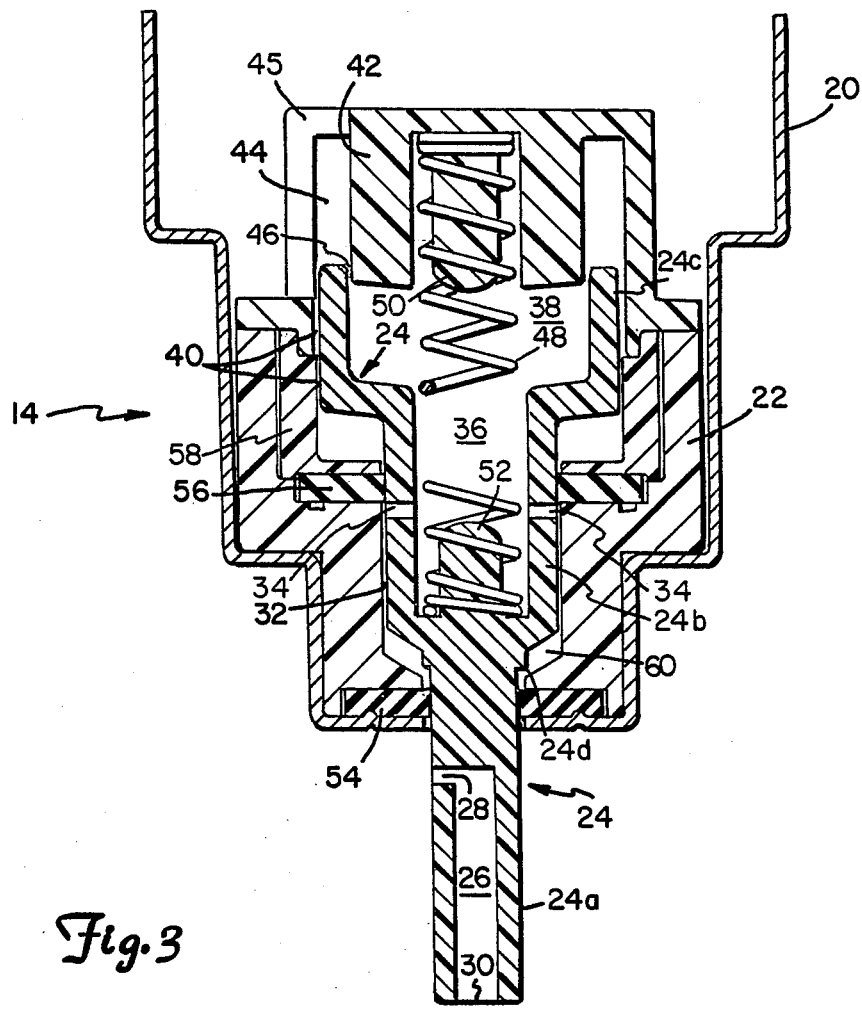
FIG. 3 is a cross-sectional view of the metering valve of FIG. 2, with the valve being in a filling or metering position.

Referring still to FIG. 3, the aerosol formulation enters the filling volume of metering chamber 60 in the following manner. Formulation from the aerosol container 12 (see FIG. 1) is introduced through piston port 44 and into the hollow interior 38 and 36 of internal valve stem portions 24c and 24b, respectively. The aerosol formulation then passes through passageways 34 and flows through narrow annular passageway 32 into the filling volume of metering chamber 60 immediately upon creation of the filling volume. Thus, as valve stem 24 is moved from the resting position shown in FIG. 2 to the filling position shown in FIG. 3, aerosol formulation is immediately provided from the aerosol container to the filling volume formed in metering chamber 60 as the valve stem moves upwardly.

Figure 4:
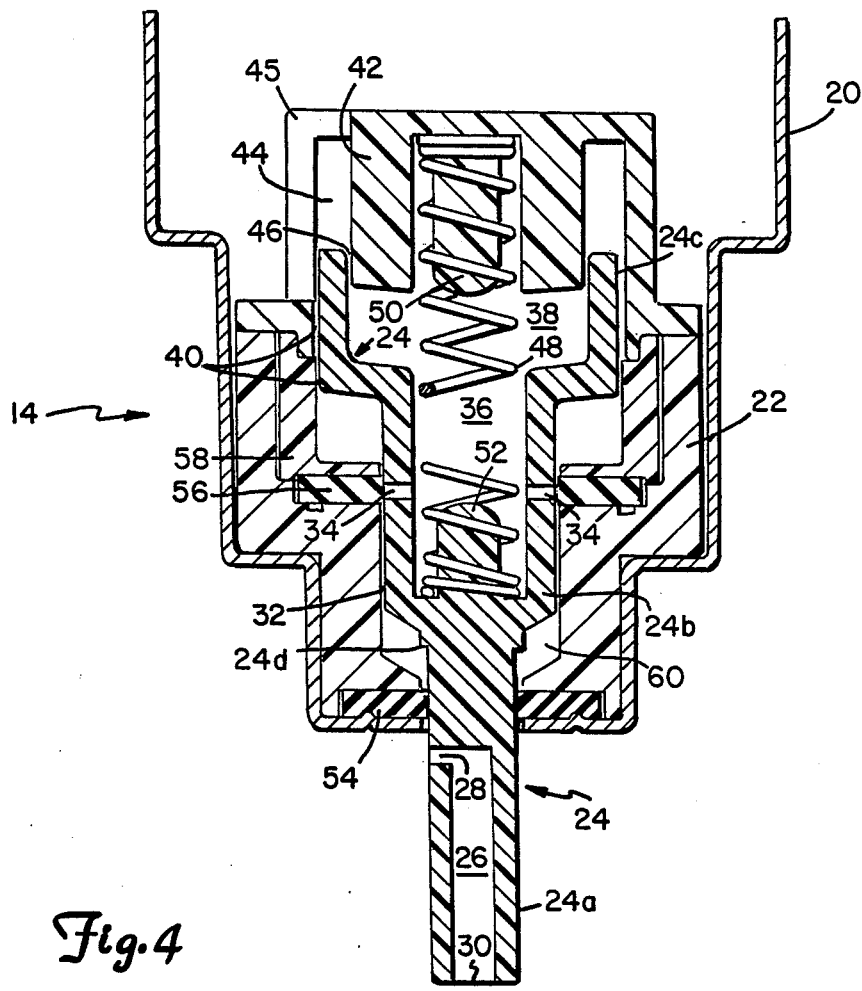
FIG. 4 is a cross-sectional view of the metering valve of FIG. 2, with the valve being in a completely filled position.

The increasing filling volume within metering chamber 60 continues to be immediately filled with the aerosol formulation as the valve stem proceeds upwardly, until passageways 34 meet passageway seal 56 at the position illustrated in FIG. 4. At this point, seal 56 precludes the entry of any further aerosol formulation from passageways 34 into annular space 32, and the filling volume of metering chamber 60 is considered completely filled or metered. As will be seen from FIG. 4, at this point, the volume of aerosol formulation within metering chamber 60 is a precisely measured amount which may be predetermined by the design dimensions of the valve body 22, valve stem 24, and the other valve components.

Thus, at the completely filled position shown in FIG. 4, metering chamber 60 is filled with a complete dosage of the aerosol formulation, which is ready to be dispensed. At the same time, further supply of the aerosol formulation from the aerosol container is cut off by the action of seal 56.

Figure 5:
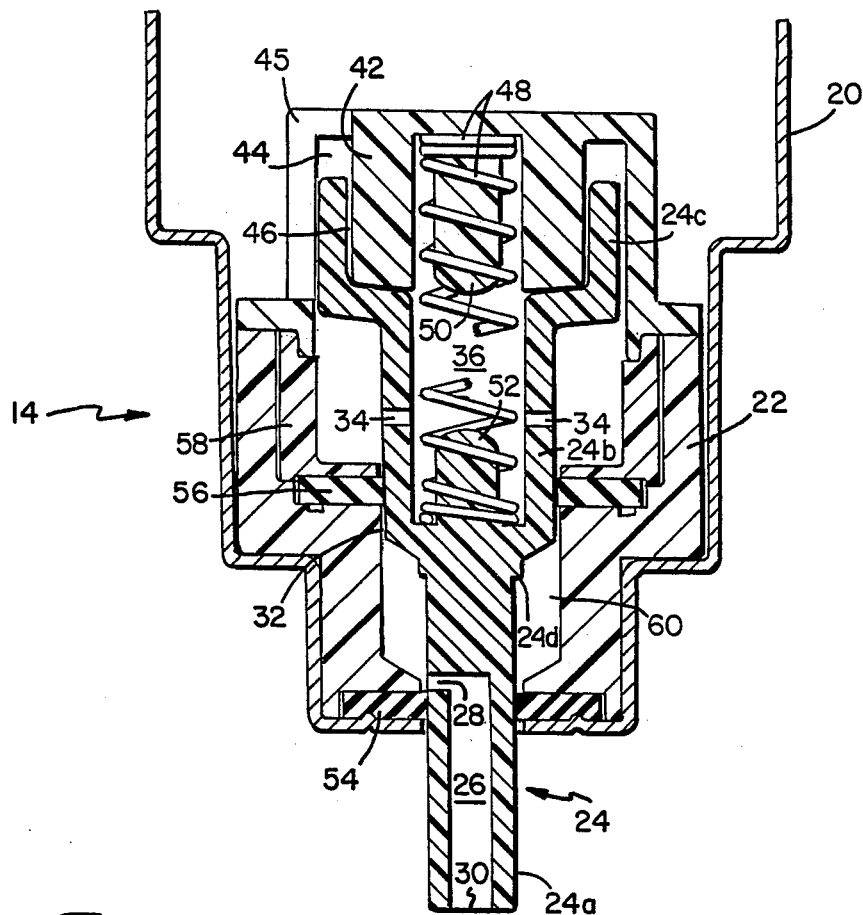
FIG. 5 is a cross-sectional view of the metering valve of FIG. 2, with the valve being in a firing or discharging position.

In order to discharge the metered dosage of aerosol formulation within metering chamber 60, valve stem 24 is further depressed so as to attain the position shown in FIG. 5. Thus, FIG. 5 represents the firing or discharging position for releasing the aerosol formulation.

As seen in FIG. 5, as valve stem 24 is inserted further into valve housing 20, the radial opening 28 of bore 26 passes through the seal 54 and comes into fluid communication with metering chamber 60. At that moment, the aerosol formulation within metering chamber 60 is immediately released into opening 28 and passes through bore 26 and out of opening 30 so as to be delivered to the patient or other desired area. After discharge of the aerosol formulation, the user releases the valve stem 24 which returns to its original resting position shown in FIG. 2 by the biasing action of resilient spring 48. It should be noted that, during discharge of the aerosol formulation from metering chamber 60 when the valve stem is positioned as shown in FIG. 5, seal 56 continues to isolate the bulk aerosol formulation within the aerosol container from the metered dose within metering chamber 60.

As will be appreciated by those skilled in the art, the successive positionings of valve stem 24 shown in FIGS. 2, 3, 4, and 5 are all accomplished during the brief moment when the user depresses and then releases valve stem 24. Hence, the actual positioning of valve stem 24 through the various stages shown in FIGS. 2, 3, 4, and 5, and subsequently back to FIG. 2, occurs in an instant. Similarly, the formation, filling, and emptying of the metering chamber occurs equally rapidly. As a result, there is virtually no aerosol formulation standing in the metering chamber between dosages, and the metering chamber is full of aerosol formulation only during the brief moment immediately preceding discharge of the aerosol formulation from the metering chamber.

During the progressively upward positioning of valve stem 24 depicted in FIGS. 2, 3, 4, and 5, it will be noted that second internal portion 24c acts as a cylinder as it approaches and engages piston 42. As the valve stem 24 travels upwardly, the available area between piston 42 and the interior 38 of second internal portion 24c becomes compressed, thereby providing a positive filling pressure within the valve. Thus, as the valve stem 24 is moved between the resting position shown in FIG. 2 and the completely filled position shown in FIG. 4, the piston provides a positive pressure for encouraging the aerosol formulation into metering chamber 60. In this regard, the positive fill pressure provided by the piston 42 ensures that the metering chamber 60 is immediately filled with the aerosol formulation upon its creation. Further, with the aerosol formulation under pressure within hollow interior 36 and 38, annular space 46 provides an escape route for excess aerosol formulation to pass back into the aerosol container until further needed.

From the foregoing, it will be appreciated that the metering valves and methods of the present invention serve to solve the problems which have plagued the metering valve art up to this point. For example, the metering valve of FIGS. 1-5 of the present invention does not need to be primed, nor is it capable of losing its prime. Because the metering chamber 60 is created and filled only upon actuation of valve stem 24, there is no aerosol formulation stored in the metering chamber in between dosages, and loss of formulation during standing and/or storage is completely avoided.

Further, erratic delivery of suspension formulations is also avoided. Where the aerosol formulation is a suspension, the aerosol container is merely shaken up prior to usage, and only freshly mixed formulation enters the metering chamber when the valve stem 24 is depressed. Again, since no aerosol formulation is stored in the metering chamber in between dosages, settling of various chemical components into and out of the metering chamber is completely avoided. As a result, a reliable dosage of precise composition and concentration is delivered each time the valve stem is depressed.

Furthermore, the unique design of the metering valves of FIGS. 1-5 of the present invention virtually eliminates tail-off and reduces holdup to an amount of one dose or less. Because metering chamber 60 is formed at the lowest end of valve 14 when in the position shown in FIGS. 3-5, and because of the continual action of piston 42, metering chamber 60 fills completely even when the container has only a few more doses left in it. Thus, the problem of tail-off is significantly avoided, and even the last dosages delivered are precise and complete.

Moreover, the last portion of aerosol formulation remaining within the aerosol container will continue to seek the bottom of the metering valve 14 so that the most formulation which could be wasted is less than one dose, as defined by the metering chamber 60 at the lowest portion of metering valve 14. Hence, the prior art problem of multiple dosage holdup is also substantially eliminated.

As will be appreciated, the valve body 22, valve stem 24, and other valve components may be configured so as to define metering chambers of various sizes as needed. Since the metered dose is precisedly defined by the size of the metering chamber when the valve stem is in the position shown in FIG. 4, the amount of dosage delivered by a given metering valve can be easily controlled by properly designing the dimensions of the valve components to form a metering chamber of the appropriate size. Furthermore, metering valves having different capacities can be manufactured merely by altering the relative position of passageways 34 along the wall of first internal portion 24b, so as to define a smaller or larger volume within the metering chamber when the passageways 34 reach seal 56 at the position shown in FIG. 4.

Reference will now be made to FIGS. 6-10 which illustrate other preferred embodiments of the metering valves of the present invention. The alternative embodiments shown in FIGS. 6-10 include various means for allowing the aerosol container to be pressure filled through the metering valve.

Figure 6:
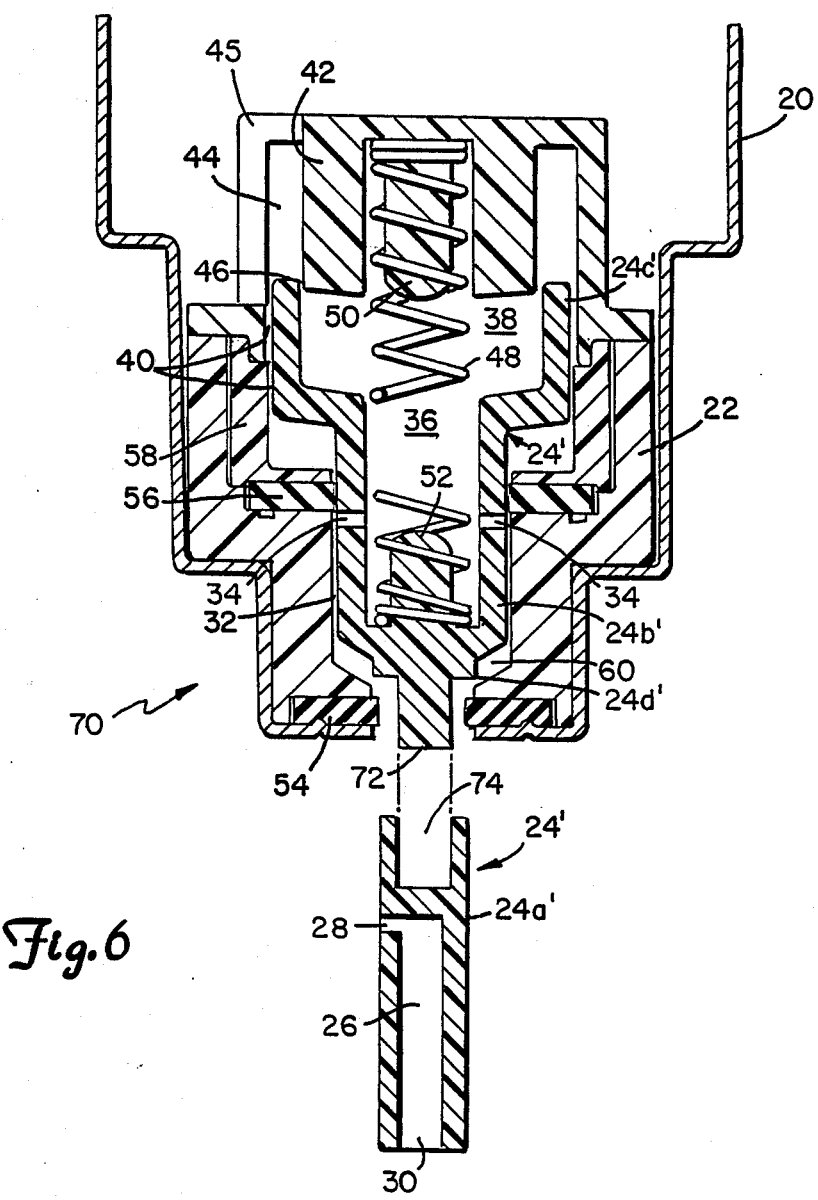
FIG. 6 is a cross-sectional view of another presently preferred embodiment of a metering valve in accordance with the present invention, with the valve stem being configured as a two-part structure, the external portion of the valve stem being disconnectable from the internal portion of the valve stem in order to allow for pressure filling through the metering valve.

Referring first to FIG. 6, an alternative embodiment of a metering valve within the scope of the present invention is illustrated which incorporates a disconnectable valve stem. As seen in FIG. 6, this metering valve, generally designated 70, includes a valve stem 24' which has an external portion 24a', a first internal portion 24b', and a second internal portion 24c', similar to the embodiment of FIGS. 2-5. However, in metering valve 70 of FIG. 6, the external portion 24a' of the valve stem is disconnectable from the first internal portion 24b' of the valve area. For this purpose a coupling extension 72 is formed at the bottom of first internal portion 24b', while a correspondingly shaped recess 74 is formed in the upper end of external portion 24a'. With this configuration, external portion 24a' can be snap-fit onto the end of first internal portion 24b' by engaging coupling extension 72 into recess 74. In this engagement, metering valve 70 of FIG. 6 has virtually the same configuration and functions virtually the same as metering valve 14 of FIGS. 2-5.

As mentioned, the disconnectable external portion 24a' allows for pressure filling of the aerosol container through metering valve 70. To do this, external portion 24a' is disconnected from first internal portion 24b', and a conventional pressure nozzle (not shown), connected to a pressurized supply of aerosol formulation (not shown), is positioned around the opening formed between extension 72 and gasket 54 and valve housing 20. The pressure nozzle also serves to upwardly displace valve stem 24 so that it assumes the approximate position shown in FIG. 6. With the pressure nozzle positioned around the bottom opening of valve 70 and with internal portions 24b' and 24c' positioned as shown in FIG. 6, aerosol formulation under pressure can be released from the pressure nozzle and flow through the metering valve 70 into the aerosol container.

The flow of aerosol formulation from the pressure nozzle into the aerosol container is as follows. First, the pressurized aerosol formulation leaves the pressure nozzle and enters into chamber 60 which has been formed by the upward displacement of internal portions 24b' and 24c'. The pressurized aerosol formulation flows from chamber 60 into narrow annular passageway 32, and through passageways 34 into the hollow interior 36 and 38 of the first and second internal portions 24b' and 24c', respectively. From the hollow interior 36 and 38, the pressurized aerosol formulation next passes through narrow annular passageway 46 and through piston port 44 into the aerosol container.

Thus, by removing disconnectable external portion 24a', metering valve 70 can be pressure filled from an external source. This allows for complete assembly of the metering valve with the aerosol container before filling the container, and/or for refilling and reuse of the aerosol container after the aerosol formulation in the container has once been depleted.

Figure 7:
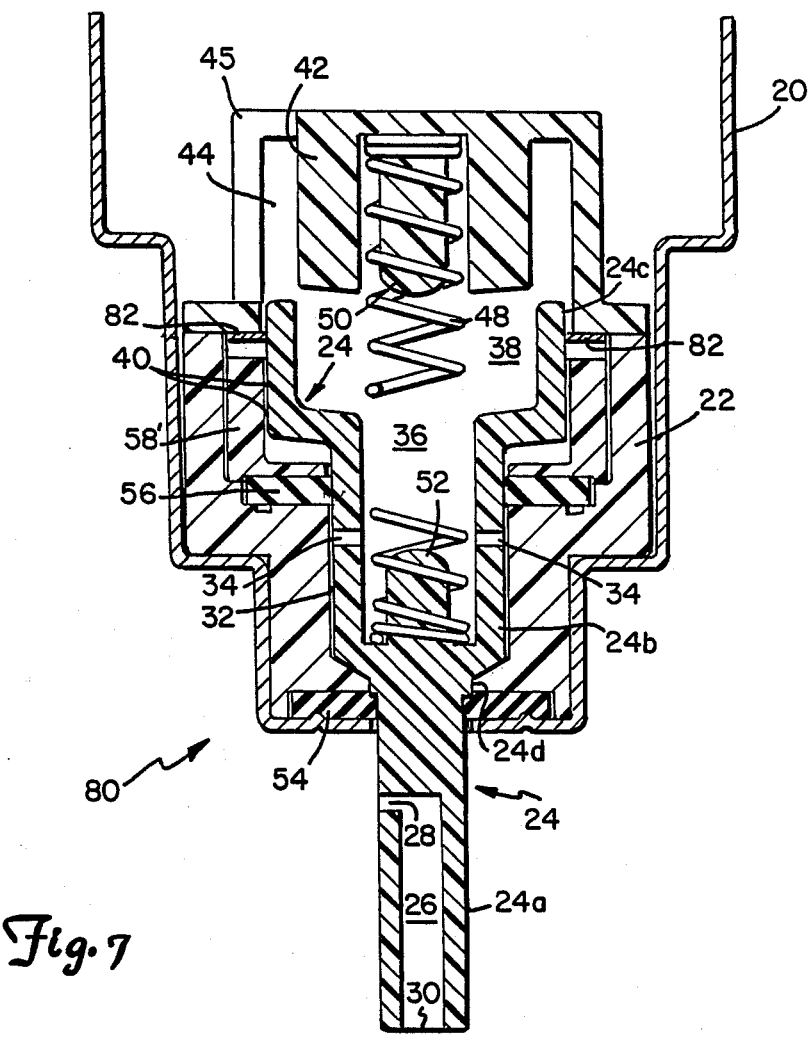
FIG. 7 is a cross-sectional view of another presently preferred embodiment of a metering valve in accordance with the present invention, incorporating resilient means for allowing displacement of certain parts of the metering valve so as to provide another method for pressure filling through the metering valve.
Figure 8:
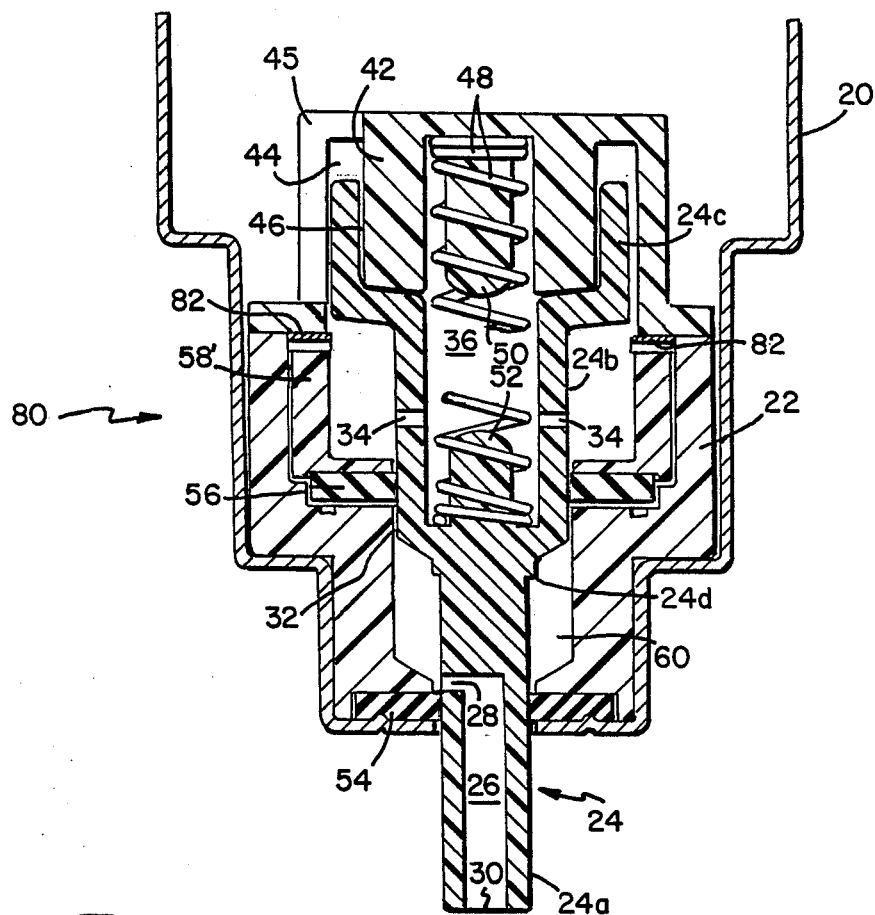
FIG. 8 is a cross-sectional view of the embodiment of FIG. 7 showing the relative position of the various components of the metering valve during pressure filling.

Another alternative embodiment which allows for pressure filling of the metering valve is generally designated 80 in FIGS. 7 and 8. Metering valve 80 of FIGS. 7 and 8 is substantially identical to metering valve 14 of FIGS. 2-5 with the following exceptions. Gasket retainer 58' of metering valve 80 is configured so as to have slightly less height than gasket retainer 58 of metering valve 14, as may be seen, for example, by comparing FIGS. 2 and 7. By so reducing the height of gasket retainer 58', an annular space is created between gasket retainer 58' and piston 42. As seen in FIG. 7, this space is occupied by resilient means such as a wave spring 82 which serves to bias gasket retainer 58' and gasket 56 in a direction away from piston 42. Thus, in the resting or inoperational position of valve 80 shown in FIG. 7, wave spring 82 serves to hold gasket retainer 58' and gasket 56 snugly against valve body 22 so as to form a fluid tight seal between gasket 56 and valve body 22.

However, with the placement of wave spring 82 above gasket retainer 58', the gasket retainer 58'/gasket 56 assembly may be displaced in an upward direction by applying a positive pressure underneath gasket 56 as best illustrated in FIG. 8. Thus, FIG. 8 shows how metering valve 80 may be pressure filled.

Referring now to the pressure filling position shown in FIG. 8, a pressure nozzle (not shown) is positioned around external portion 24a of the valve stem and the valve stem is displaced upwardly to the position shown in FIG. 8. Pressurized aerosol formulation is released from the pressurized nozzle and flows through bore 26 and into chamber 60. Because of the displacability of the gasket retainer 58'/gasket 56 assembly, the pressurized aerosol formulatoin flows through annular passageway 32 and under gasket 56, lifting gasket 56 off of valve body 22 as shown in FIG. 8. Hence, the pressurized aerosol formulation is able to flow from annular passageway 32 to underneath gasket 56, between a narrow space formed between valve body 22 and gasket retainer 58', through the space occupied by wave spring 82, into the space between gasket retainer 58'and first internal portion 24b, and finally through piston port 44 into the aerosol container.

Thus, it will be appreciated that wave spring 82 provides a means for pressure filling the aerosol container through metering valve 80. Once the aerosol container has been filled in accordance with the foregoing procedure, the pressure nozzle is removed from around external portion 24a of the valve stem, and the valve stem 24 returns to its original resting position shown in FIG. 7 by the biasing action of spring 48. At the same time, the gasket retainer 58'/gasket 56 assembly returns to its original resting position shown in FIG. 7 by the biasing action of wave spring 82.

It will be appreciated that wave spring 82 is merely one example of means for biasing the gasket retainer 58'/gasket 56 assemby against valve body 22, and that other biasing structure could be used for this purpose. For example, the gasket retainer 58 of FIG. 2 could itself be fabricated so as to be resilient and provide the necessary biasing action. Thus, any other suitable means for biasing the gasket retainer/gasket assembly against the valve body may be used in accordance with the present invention.

Figure 9:
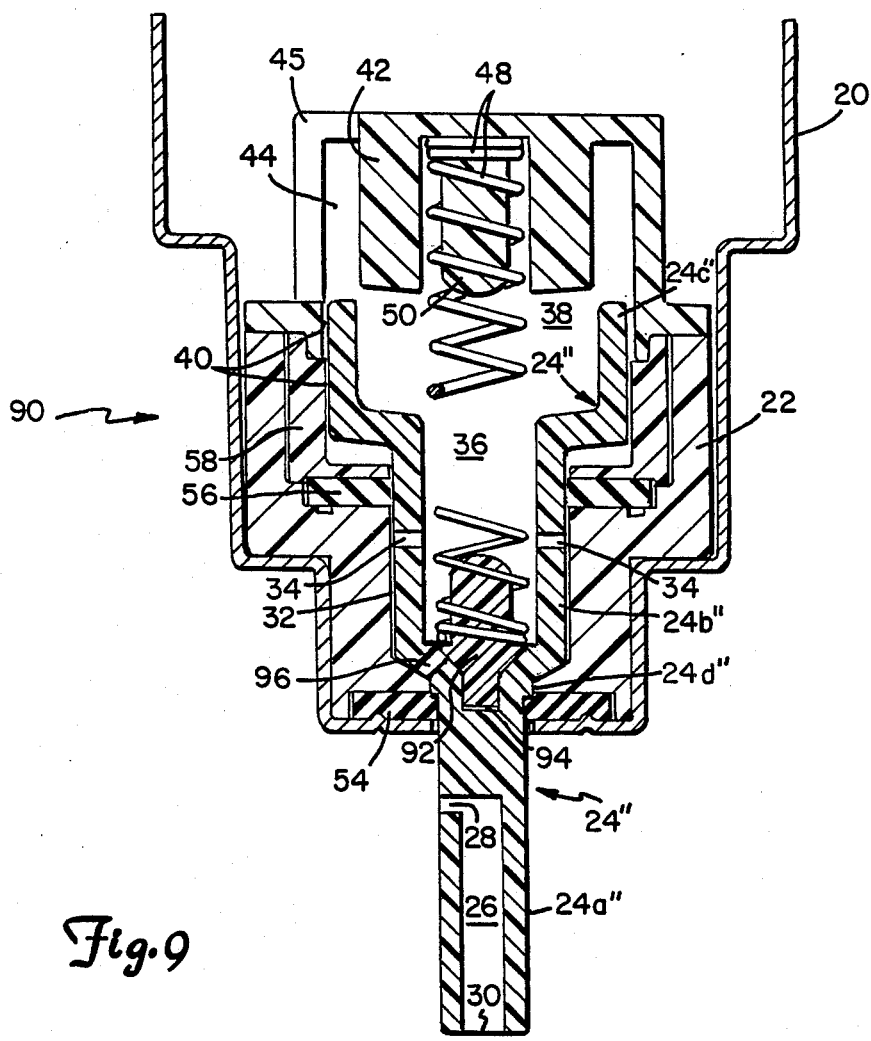
FIG. 9 is a cross-sectional view of still another presently preferred embodiment of a metering valve in accordance with the present invention, incorporating a plug within the interior of the valve stem and a bore formed in the sidewall of the valve stem so as to provide yet another means for pressure filling through the metering valve.
Figure 10:
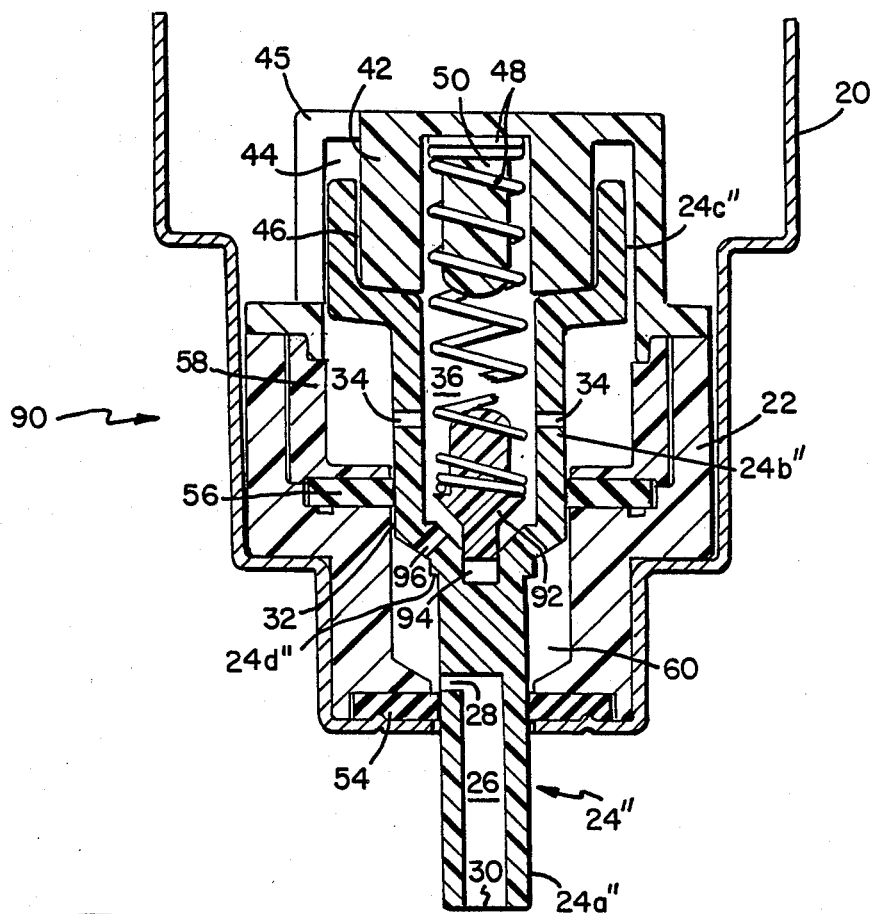
FIG. 10 is a cross-sectional view of the embodiment of FIG. 9 showing the relative position of the component parts of the metering valve during pressure filling.

Still another preferred embodiment of a metering valve within the scope of the present invention, generally designated 90, is shown in FIGS. 9 and 10. Metering valve 90 incorporates features which provide yet another means for pressure filling in accordance with the present invention.

As seen for example in FIG. 9, metering valve 90 is identical to metering valve 14 of FIGS. 2-5 with the following exceptions. Metering valve 90 includes a resilient plug 92 positioned within hollow interior 36 so as to assume the resting position shown in FIG. 9. In this position, the end of resilient plug 92 sits into a correspondingly shaped recess 94 formed in first internal portion 24b''. Furthermore, a port 96 is formed in the wall of first internal portion 24b''. Advantageously, since port 96 is positioned as shown in FIG. 9 such that seal 54 is the only structure used to isolate valve stem 24 from the outside environment, port 96 alone does not present the opportunity for any leakage from the valve. As will be recognized, the top portion of resilient plug 92 of metering valve 90 substitutes for nipple 52 of metering valve 14, and serves to secure the bottom end of spring 48. The use of metering valve 90 to pressure fill an aerosol container will now be explained with reference to FIG. 10.

As with the other pressure filling embodiments, a pressure nozzle (not shown) is positioned around external portion 24a'', and the valve stem 24'' is displaced upwardly to the position shown in FIG. 10. With metering valve 90 positioned as shown in FIG. 10, the pressurized aerosol formulation flows from the pressure nozzle through bore 26 and into chamber 60. The formulation then flows from chamber 60 through port 96 and into hollow interior 36 by the upper displacement of resilient plug 92 against spring 48. The pressurized aerosol formulation then flows from hollow 36 through passageways 34 and into the space formed between gasket retainer 58 and first internal portion 24b''. The pressurized formulation then continues up through piston port 44 and into the aerosol container. Once the aerosol container has been filled, the pressure nozzle is removed and the biasing action of sp ring 48 serves to restore resilient plug 92 and valve stem 24'' back to the position shown in FIG. 9.

It will be appreciated that the various pressure filling features shown in the embodiments of FIGS. 6-10 are purely optional, and may be used where it is desired to pressure fill aerosol containers incorporating the metering valves of the present invention. However, it will be appreciated that there are other methods besides pressure filling which are well known in the art and which may be used to fill the aerosol containers with pressurized aerosol formulation in accordance with the present invention.

For example, a cold fill procedure may be used to fill the aerosol container before it is crimped onto the end of the metering valve. For this purpose, the propellant and formulation to be administered are mixed and poured into the aerosol container 12 of the embodiment of FIG. 1 at a temperature which is low enough to place the aerosol formulation in a liquid state, for example, about −60° C. Subsequently, the top end of metering valve 14 is crimped onto aerosol container 12 as shown in FIG. 1, and the aerosol formulation is allowed to warm up to room temperature. In this way, the aerosol container is filled prior to its assembly with the metering valve.

It will be appreciated that the foregoing methods for cold filling or pressure filling aerosol containers through the metering valves of the present invention are given by way of example only, and are not meant to be comprehensive. Thus, as stated, other filling techniques are known in the art and may be practiced in aerosol container devices employing metering valves which are within the scope of the present invention.

The precise choice of materials used in the manufacture of the metering valves of the present invention is not critical and is well within the skill of the art; virtually any suitable materials may be used for this purpose. For example, plastic and/or metal parts may be used for virtually all of the components of the metering valves of the present invention. However, it is often preferable to manufacture spring 48 and valve housing 20 of metal so as to provide for the proper biasing action of spring 48 and for maximum protection of the internal components of the metering valve 14 from the environment. Moreover, elastomeric materials are often preferred for manufacturing gaskets 54 and 56. Wave spring 82 may be made of either plastic or metal, so long as resiliency is preserved.

The metering valves of the present invention may be used to dispense virtually any pressurized fluids. For example, besides aerosols, the present invention could also be used to dispense self pressurized fluids, e.g., fluids that have a high enough vapor pressure to create a positive pressure within the metering valve. Moreover, if desired, the metering valves of the present invention could also be used to dispense fluids which are not pressurized.

For example, gravity activation could be used to dispense a non-pressurized fluid if venting means were provided so as to allow the fluid to exit from the valve. One example of such possible venting means would be to shape bore 26 of FIGS. 2-5 as a T (not shown), such that there would be two openings (corresponding to opening 28 in FIGS. 2-5) in the side wall of external portion 24a. Subsequently, in the dispensing position of FIG. 5, the fluid could be gravity dispensed through one of the openings in the side wall while air would enter the other opening so as to occupy the area within chamber 60 vacated by the fluid dispensed.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A valve for delivering a predetermined amount of a fluid, comprising:
   a valve housing;
   a valve stem movably mounted within said valve housing between a first position and a second position, said valve stem in said second position defining with said valve housing a metering chamber dimensioned to receive said predetermined amount of fluid, said valve stem in said first position occupying substantially the entire volume of said metering chamber, said valve stem having a first portion which is generally external to said valve housing and a second portion which is generally internal to said valve housing when said valve stem is in the first position, said second position being configured so as to occupy substantially the entire volume of said metering chamber when said valve stem is in the first position, said first portion being configured such that, when said valve stem is in the second position, at least a part of said first portion is positioned within said valve housing so as to form said metering chamber between said valve stem and said valve housing;
   means for supplying fluid to said metering chamber as said metering chamber is formed; and
   means for releasing the fluid from said metering chamber.

2. A valve as defined in claim 1 wherein said second portion of said valve stem has a larger circumference than said first portion of said valve stem.

3. A valve as defined in claim 1 further comprising means for providing a fluid tight seal between said valve housing and said first portion of said valve stem.

4. A valve as defined in claim 1 further comprising means for biasing said valve stem in a direction towards the first position.

5. A valve as defined in claim 4 wherein said biasing means comprises a spring positioned within the interior of said valve stem.

6. A valve as defined in claim 1 wherein said supplying means comprises a receptacle capable of containing the fluid to be delivered, said receptacle being mounted to said valve housing so as to be in fluid communication with said metering chamber when said metering chamber is being filled.

7. A valve as defined in claim 1 further comprising a discharge piece positioned around said releasing means so as to receive fluid discharged from said releasing means, said discharge piece being adapted for insertion into a body cavity of a patient to whom the fluid is to be administered.

8. A valve as defined in claim 1 wherein said valve stem is also movable to a third position and wherein said releasing means comprises a bore formed in said first portion of said valve stem, said bore being configured so as to provide fluid communication between said metering chamber and the area outside of said first portion when said valve stem is in the third position.

9. A valve as defined in claim 8 wherein said bore is L-shaped with one end of said bore communicating with said metering chamber through a side wall of said first portion and with the other end of said bore communicating with the area outside of said first portion when said valve stem is in the third position.

10. A valve as defined in claim 1 wherein said second portion of said valve stem is hollow and further comprising means for providing fluid communication between the hollow of said second portion and said metering chamber while said metering chamber is being filled with fluid.

11. A valve as defined in claim 10 wherein said fluid communication providing means comprises at least one passageway formed in a wall of said second portion of said valve stem.

12. A valve as defined in claim 11 further comprising a passageway seal mounted within said valve housing, said passageway seal being capable of occluding said passageway when said valve stem is in the second position.

13. A valve as defined in claim 12 further comprising means for biasing said passageway seal in a direction towards said metering chamber, said biasing means being displaceable in a direction away from said metering chamber so as to allow for pressure filling of the valve underneath said passageway seal.

14. A valve as defined in claim 10 wherein:
   said supplying means comprises a piston mounted within said valve housing; and
   said valve stem further comprises a hollow third portion which is internal to said valve housing and which is in fluid communication with said second portion, said third portion beign configured so as to receive said piston as said valve stem is moved theretowards and thereby create a positive filling pressure within said metering chamber.

15. A valve as defined in claim 14 wherein said third portion of said valve stem has a larger circumference than said second portion of said valve stem.

16. A valve as defined in claim 1 wherein said first portion of said valve stem is detachable from said second portion of said valve stem so as to allow for pressure filling of the valve.

17. A valve as defined in claim 1 further comprising:
   a filling port formed in a wall of said second portion of said valve stem, said filling port allowing for pressure filling of the valve; and
   means for sealing said filling port when the valve is not being pressure filled.

18. A valve for delivering a predetermined amount of a fluid, comprising:
   a valve housing;
   a valve stem movably mounted within said valve housing between a first position, a second position, and a third position such that said valve stem moves sequentially from the first position to the second position to the third position as the valve stem is depressed in a single direction, said valve stem in said second position defining with said valve housing a metering chamber dimensioned to receive said predetermined amount of fluid, said valve stem in said first position occupying substantially the entire volume of said metering chamber;
   means for supplying fluid to said metering chamber; and
   means for releasing the fluid from said metering chamber when said valve stem arrives at the third position.

19. A valve as defined in claim 18 wherein said valve stem has a first portion which is generally external to said valve housing and a second portion which is generally internal to said valve housing when said valve stem is in the first position, said second portion being configured so as to occupy substantially the entire volume of said metering chamber when said valve stem is in the first position, said first portion being configured such that, when said valve stem is in the second position, at least a part of said first portion is positioned within said valve housing so as to form said metering chamber between said valve stem and said valve housing.

20. A valve as defined in claim 18 wherein said releasing means comprises a fluid outlet port formed in said valve stem, which fluid outlet port comes into fluid communication with said metering chamber when said valve stem arrives at the third position.

21. A valve as defined in claim 19 wherein said second portion of said valve stem has a larger circumference than said first portion of said valve stem.

22. A valve as defined in claim 19 wherein said releasing means comprises a bore formed in said first portion of said valve stem, said bore being configured so as to provide fluid communication between said metering chamber and the area outside of said first portion when said valve stem is in the third position, said bore being L-shaped with one end of said bore communicating with said metering chamber through a side wall of said first portion and with the other end of said bore communicating with the area outside of said first portion when said valve stem is in the third position.

23. A valve as defined in claim 19 wherein said second portion of said valve stem is hollow and further comprising means for providing fluid communication between the hollow of said second portion and said metering chamber while said metering chamber is being filled with fluid.

24. A valve as defined in claim 23 wherein said fluid communication providing means comprises at least one passageway formed in a wall of said second portion of said valve stem.

25. A valve as defined in claim 24 further comprising a passageway seal mounted within said valve housing, said passageway seal being capable of occluding said passageway when said valve stem is in the second position.

26. A valve as defined in claim 25 further comprising means for biasing said passageway seal in a direction towards said metering chamber, said biasing means being displaceable in a direction away from said metering chamber so as to allow for pressure filling of the valve underneath said passageway seal.

27. A valve as defined in claim 23 wherein:
said supplying means comprises a piston mounted within said valve housing; and
said valve stem further comprises a hollow third portion which is internal to said valve housing and which is in fluid communication with said second portion, said third portion being configured so as to receive said piston as said valve stem is moved theretowards and thereby create a positive filling pressure within said metering chamber.

28. A valve as defined in claim 27 wherein said third portion of said valve stem has a larger circumference than said second portion of said valve stem.

29. A valve as defined in claim 19 further comprising means for providing a fluid tight seal between said valve housing and said first portion of said valve stem.

30. A valve as defined in claim 19 wherein said first portion of said valve stem is detachable from said second portion of said valve stem so as to allow for pressure filling of the valve.

31. A valve as defined in claim 19 further comprising:

a filling port formed in a wall of said second portion of said valve stem, said filling port allowing for pressure filling of the valve; and
means for sealing said filling port when the valve is not being pressure filled.

32. A valve as defined in claim 18 further comprising means for biasing said valve stem in a direction towards the first position.

33. A valve as defined in claim 32 wherein said biasing means comprises a spring positioned within the interior of said valve stem.

34. A valve as defined in claim 18 wherein said supplying means comprises a receptacle capable of containing the fluid to be delivered, said receptacle being mounted to said valve housing so as to be in fluid communication with said metering chamber when said metering chamber is being filled.

35. A valve as defined in claim 18 further comprising a discharge piece positioned around said releasing means so as to receive fluid discharged from said releasing means, said discharge piece being adapted for insertion into a body cavity of a patient to whom the fluid is to be administered.

36. A valve as defined in claim 18 wherein said fluid supplying means comprises means for supplying fluid to said metering chamber as said metering chamber is formed.

37. A valve for delivering a predetermined amount of a fluid, comprising:
a valve housing;
a valve stem movably mounted within said valve housing between a first position, a second position, and a third position, said valve stem having a first portion which is generally external to said valve housing and a second portion which is generally internal to said valve housing when said valve stem is in the first position, said valve stem being configured such that, when said valve stem is in the second position, at least a part of said first portion is positioned within said valve housing so as to define a metering chamber between said valve stem and said valve housing, said metering chamber being dimensioned to receive said predetermined amount of fluid, said second portion of said valve stem being configured so as to occupy substantially the entire volume of said metering chamber when said valve stem is in the first position;
means for supplying fluid to said metering chamber as said metering chamber is formed; and
means for releasing the fluid from said metering chamber, said releasing means comprising a bore formed in said first portion of said valve stem, said bore being configured so as to provide fluid communication between said metering chamber and the area outside of said first portion when said valve stem is in the third position.

38. A valve as defined in claim 37 wherein said bore is L-shaped with one end of said bore communicating with said metering chamber through a side wall of said first portion and with the other end of said bore communicating with the area outside of said first portion when said valve stem is in the third position.

39. A valve as defined in claim 37 wherein said valve stem moves sequentially from the first position to the second position to the third position as the valve stem is depressed in a single direction.

40. A valve for delivering a predetermined amount of a fluid, comprising:

a valve housing;

a valve stem movably mounted within said valve housing between a first position and a second position, said valve stem having a first portion which is generally external to said valve housing and a hollow second portion which is generally internal to said valve housing when said valve stem is in the first position, said valve stem being configured such that, when said valve stem is in the second position, at least a part of said first portion is positioned within said valve housing so as to form a metering chamber between said valve stem and said valve housing, said metering chamber being dimensioned to receive said predetermined amount of fluid, said second portion being configured so as to occupy substantially the entire volume of said metering chamber when said valve stem is in the first position;

means for supplying fluid to said metering chamber including means for providing fluid communication between the hollow of said second portion and said metering chamber while said metering chamber is being filled with fluid; and means for releasing the fluid from said metering chamber.

41. A valve as defined in claim 40 wherein said fluid communication providing means comprises at least one passageway formed in a wall of said second portion of said valve stem.

42. A valve as defined in claim 41 further comprising a passageway seal mounted within said valve housing, said passageway seal being capable of occluding said passageway when said valve stem is in the second position.

43. A valve as defined in claim 42 further comprising means for biasing said passageway seal in a direction towards said metering chamber, said biasing means being displaceable in a direction away from said metering chamber so as to allow for pressure filling of the valve underneath said passageway seal.

44. A valve as defined in claim 40 wherein:

said supplying means comprises a piston mounted within said valve housing; and said valve stem further comprises a hollow third portion which is internal to said valve housing and which is in fluid communication with said second portion, said third portion being configured so as to receive said piston as said valve stem is moved theretowards and thereby create a positive filling pressure within said metering chamber.

45. A valve as defined in claim 44 wherein said third portion of said valve stem has a larger circumference than said second portion of said valve stem.

46. A valve for delivering a predetermined amount of a fluid, comprising:

a valve housing;

a valve stem movably mounted within said valve housing between a first position and a second position, said valve stem hving a first portion which is generally external to said valve housing and a second portion which is generally internal to said valve housing when said valve stem is in the first position, said valve stem being configured such that, when said valve stem is in the second position, at least a part of said first portion is positioned within said valve housing so as to form a metering chamber between said valve stem and said valve housing, said metering chamber being dimensioned to receive said predetermined amount of fluid, said second portion being configured so as to occupy substantially the entire volume of said metering chamber when said valve stem is in the first position, said first portion of said valve stem being detachable from said second portion of said valve stem so as to allow for pressure filling of the valve;

means for supplying fluid to said metering chamber; and means for releasing the fluid from said metering chamber.

47. A valve for delivering a predetermined amount of a fluid, comprising:

a valve housing;

a valve stem movably mounted within said valve housing between a first position and a second position, said valve stem having a first portion which is generally external to said valve housing and a second portion which is generally internal to said valve housing when said valve stem is in the first position, said valve stem being configured such that, when said valve stem is in the second position, at least a part of said first portion is positioned within said valve housing so as to form a metering chamber between said valve stem and said valve housing, said metering chamber being dimensioned to receive said predetermined amount of fluid, said second portion being configured so as to occupy substantially the entire volume of said metering chamber when said valve stem is in the first position;

a filling port formed in a wall of said second portion of said valve stem, said filling port allowing for pressure filling of the valve;

means for sealing said filling port when the valve is not being pressure filled;

means for supplying fluid to said metering chamber; and means for releasing the fluid from said metering chamber.

48. A valve for delivering a predetermined amount of a pressurized fluid, comprising:

a valve housing;

a valve stem which is movably mounted within said valve housing between a first position and a second position, said valve stem in said second position defining with said valve housing a metering chamber dimensioned to receive said predetermined amount of pressurized fluid, said valve stem having a first portion which is generally internal to said valve housing and a second portion which is generally external to said valve housing when said valve stem is in the first position, said first portion of said valve stem being configured substantially the same as the wall of said valve housing defining said metering chamber such that, when in the first position, said first portion of said valve stem occupies substantially the entire volume of said metering chamber, said first portion of said valve stem having a larger circumference than said second portion of said valve stem such that, when said valve stem is in the second position so that at least a part of said second portion is positioned within said valve housing, said metering chamber is formed between said valve stem and said valve housing;

means for supplying pressurized fluid to said metering chamber; and means for releasing the pressurized fluid from said metering chamber after said metering chamber is filled.

49. A valve for repeatably delivering a precise amount of an aerosol formulation, comprising:
   a valve housing;
   a valve stem which is movably mounted within said valve housing between a first, second, and third position, said valve stem in said second position defining with said valve housing a metering chamber dimensioned to receive said precise amount of aerosol formulation, said valve stem comprising:
      a first portion extending through said valve housing so as to be generally exterior to said valve housing when said valve stem is in the first position;
      a second portion which is generally interior to said valve housing when said valve stem is in the first position, said second portion having a hollow interior, said second portion being adjacent said first portion and being configured substantially the same as the wall of said valve housing defining said metering chamber such that, when in the first position, said second portion occupies substantially the entire volume of said metering chamber, said second portion of said valve stem having a larger circumference than said first portion of said valve stem such that, when said valve stem is in the second position so that at least a part of said first portion is positioned within said valve housing, said metering chamber is formed between said valve stem and said valve housing; and
      a third portion which is interior to said valve housing, said third portion having a hollow interior, said third portion being adjacent said second portion such that the hollow of said third portion is in fluid communication with the hollow of said second portion, said third portion having a larger circumference than said second portion;
   at least one passageway formed in a wall of said second portion, said passageway providing for fluid communication between the hollow of said second portion and said metering chamber while said metering chamber is being filled with aerosol formulation;
   a passageway seal mounted within said valve housing, said passageway seal being capable of occluding said passageway when said valve stem is in the second position;
   means for supplying aerosol formulation to said metering chamber, said supplying means comprising a piston mounted within said valve housing, said third portion being configured so as to receive said piston as said valve stem is moved theretowards and thereby create a positive filling pressure within said meterig chamber; and
   a bore formed in said first portion for releasing the aerosol formulation from said metering chamber after said metering chamber is filled, said bore being configured so as to provide fluid communication between said metering chamber and the area outside of said first portion when said valve stem is in the third position.

50. A valve as defined in claim 49 wherein said bore is L-shaped with one end of said bore communicating with said metering chamber through a side wall of said first portion and with the other end of said bore communicating with the area outside of said first portion when said valve stem is in the third position.

51. A valve as defined in claim 49 further comprising means for providing a fluid tight seal between said valve housing and said first portion of said valve stem.

52. A valve as defined in claim 49 further comprising a spring positioned within the hollow of said valve stem so as to bias said valve stem in a direction towards the first position.

53. A valve as defined in claim 49 wherein said supplying means comprises a receptacle mounted to said valve housing so as to be in fluid communication with the hollow of said third portion of said valve stem, said receptacle being capable of containing the aerosol formulation to be delivered.

54. A valve as defined in claim 49 further comprising a mouthpiece positioned around said first portion of said valve stem so as to receive aerosol formulatoin discharged from said first portion, said mouthpiece being adapted for insertion into the mouth of a patient to whom the aerosol formulation is to be orally administered.

55. A method for delivering a predetermined amount of a fluid, comprising the steps of:
   providing a valve having a valve housing and a valve stem movably mounted within said valve housing between a first position and a second position, said valve stem having a first portion which is generally external to said valve housing and a second portion which is generalaly internal to said valve housing when said valve stem is in the first position, said valve stem in said second position defining with said valve housing a metering chamber dimensioned to receive said predetermined amount of fluid, said valve stem in said first position occupying substantially the entire volume of said metering chamber;
   positioning the valve stem in the first position such that the valve stem occupies substantially the entire volume of the metering chamber;
   moving the valve stem from the first position to the second position so as create said metering chamber;
   filling the metering chamber with fluid as it is created; and
   expelling the fluid from the metering chamber.

56. A method as defined in claim 55 wherein the volume within said metering chamber increases as said valve stem is moved from the first position towards the second position and wherein the increasing volume of the metering chamber is simultaneously filled with fluid.

57. A method for delivering a predetermined amount of a fluid, comprising the steps of:
   providing a valve having a valve housing and a valve stem movably mounted with said valve housing between a first position and a second position, said valve stem having a first portion which is generally external to said valve housing and a second portion which is generally internal to said valve housing when said valve stem is in the first position, said valve stem in said second position defining with said valve housing a metering chamber dimensioned to receive said predetermined amount of fluid;
   forming a fluid inlet port in the wall of the second portion and positioning an inlet port seal around the circumference of the second portion such that the inlet port reaches the inlet port seal when the valve stem arrives at the second position, thereby precluding further fluid from entering the metering chamber and thereby allowing the amount of fluid within the metering chamber to be precisely determined at the second position;

positioning the valve stem in the first position such that the valve stem occupies substantially the entire volume of the metering chamber;

moving the valve stem from the first position to the second position so as to create said metering chamber;

filling the metering chamber with fl uid; and expelling the fluid from the metering chamber.

58. A method for delivering a predetermined amount of a fluid, comprising the steps of:

providing a valve having a valve housing and a valve stem movably mounted within said valve housing between a first position, a second position, and a third position, said valve stem having a first portion which is generally external to said valve housing and a second portion which is generally internal to said valve housing when said valve stem is in the first position, a fluid outlet port being formed through said first portion, said valve stem in said second position defining with said valve housing a metering chamber dimensioned to receive said predetermined amount of fluid, said valve stem in said first position occupying substantially the entire volume of said metering chamber;

positioning the valve stem in the first position such that the valve stem occupies substantially the entire volume of the metering chamber;

moving the valve stem from the first position to the second position so as to create said metering chamber;

filling the metering chamber with fluid as it is created; and expelling the fluid from the metering chamber by moving the valve stem from the second position to the third position, whereby the fluid outlet port comes into fluid communication with the metering chamber when the valve stem arrives at the third position, thereby effecting release of the fluid in the metering chamber through the fluid outlet port.

59. A method for delivering a predetermined amount of a pressurized fluid, comprising the steps of:

providing a valve having a valve housing and a valve stem movably mounted within said valve housing between a first position and a second position, said valve stem in said second position defining with said valve housing a metering chamber dimensioned to receive said predetermined amount of pressurized fluid, said valve stem having a first portion which is generally internal to said valve housing and a second portion which is generally external to said valve housing when said valve stem is in the first position, the first portion having a larger circumference than the second portion;

positioning the valve stem in the first position such that the first portion occupies substantially the entire volume of the metering chamber;

moving the valve stem from the first position to the second position so as to insert at least a part of the second portion into the valve housing and thereby create the metering chamber between the valve stem and the valve housing;

filling the metering chamber with pressurized fluid immediately upon its creation; and expelling the pressurized fluid from the metering chamber after the volume within the metering chamber has reached the predetermined amount.

60. A valve for delivering a predetermined amount of a fluid, comprising:

a valve housing;

a valve stem movably mounted within said valve housing between a first position and a second position, said valve stem in said second position defining with said valve housing a metering chamber dimensioned to receive said predetermined amount of fluid, said valve stem in said first position occupying substantially the entire volume of said metering chamber;

means for biasing said valve stem in a direction towards the first position, said biasing means comprising a spring positioned within the interior of said valve stem;

means for supplying fluid to said metering chamber as said metering chamber is formed; and means for releasing the fluid from said metering chamber.

61. A valve for delivering a predetermined amount of a fluid, comprising:

a valve housing;

a valve stem movably mounted within said valve housing between a first position and a second position, said valve stem in said second position defining with said valve housing a metering chamber dimensioned to receive said predetermined amount of fluid, said valve stem in said first position occupying substantially the entire volume of said metering chamber;

means for supplying fluid to said metering chamber as said metering chamber is formed;

means for releasing the fluid from said metering chamber; and a discharge piece positioned around said releasing means so as to receive fluid discharged from said releasing means, said discharge piece being configured for insertion into a body cavity of a patient to whom the fluid is to be administered.

* * * * *

UNITED STATES PATENT AND TRADEMARK OFFICE
CERTIFICATE OF CORRECTION

Page 1 of 2

PATENT NO. : 4,819,834

DATED : April 11, 1989

INVENTOR(S) : Charles G. Thiel

It is certified that error appears in the above-identified patent and that said Letters Patent is hereby corrected as shown below:

```
Col. 1, line 35, "aersol" should read --aerosol--.
Col. 1, line 42, "formulaton" should read --formulation--.
Col. 1, line 60, "formulatoin" should read --formulation--.
Col. 3, line 32, "of" should read --or--.
Col. 4, line 45, "does" should read --dose--.
Col. 4, line 50, "medicatons" should read --medications--.
Col. 5, line 61, "fro m" should read --from--.
Col. 10, line 53, delete the word "up".
Col. 11, line 16, "precisedly" should read --precisely--.
Col. 11, line 45, delete "area" and insert therefor --stem--.
Col. 12, line 50, "po rtion" should read --portion--.
Col. 12, line 56, "formulatoin" should read --formulation--.
Col. 13, line 60, "sp ring" should read --spring--.
Col. 15, line 19, "second position" should read --second portion--.
Col. 16, line 28, "beign" should read --being--.
Col. 19, line 59, "hving" should read --having--.
Col. 21, line 57, "meterig" should read --metering--.
Col. 22, line 18, "formulatoin" should read --formulation--.
Col. 22, line 30, "generalaly" should read --generally--.
```

UNITED STATES PATENT AND TRADEMARK OFFICE
CERTIFICATE OF CORRECTION

PATENT NO. : 4,819,834

DATED : April 11, 1989

INVENTOR(S) : Charles G. Thiel

It is certified that error appears in the above-identified patent and that said Letters Patent is hereby corrected as shown below:

Col. 22, line 55, "with" should read --within--.
Col. 23, line 12, "fl uid" should read --fluid--.

Signed and Sealed this

Fourteenth Day of November, 1989

*Attest:*

JEFFREY M. SAMUELS

*Attesting Officer*   *Acting Commissioner of Patents and Trademarks*